United States Patent
Lazzari et al.

(10) Patent No.: US 6,596,461 B1
(45) Date of Patent: Jul. 22, 2003

(54) PIPERAZINONE DERIVATIVES

(75) Inventors: Dario Lazzari, Bologna (IT); Mirko Rossi, San Lazzaro di Savena (IT); Graziano Zagnoni, Vergato (IT); Alessandro Zedda, Basel (CH); Valerio Borzatta, Bologna (IT); Stephen Mark Andrews, New Fairfield, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/856,574

(22) PCT Filed: Nov. 11, 1999

(86) PCT No.: PCT/EP99/08679

§ 371 (c)(1),
(2), (4) Date: May 22, 2001

(87) PCT Pub. No.: WO00/31069

PCT Pub. Date: Jun. 2, 2000

(30) Foreign Application Priority Data

Nov. 24, 1998 (EP) .............................. 98811159

(51) Int. Cl.$^7$ .............................. G03C 1/73; G03C 1/76; C07D 403/02; C07D 241/02; C08G 73/06; C08K 5/3492

(52) U.S. Cl. .............................. 430/270.1; 430/271.1; 430/273.1; 430/281.1; 430/286.1; 430/287.1; 430/372; 430/512; 430/551; 430/905; 430/906; 430/907; 544/357; 544/379; 544/383; 544/198; 544/209; 544/212; 528/423; 524/100; 524/102; 252/401; 252/403; 252/405

(58) Field of Search .............................. 544/357, 379, 544/383, 198, 209, 212; 528/423; 252/401, 403, 405; 430/270.1, 271.1, 273.1, 281.1, 286.1, 287.1, 905, 906, 907, 551, 372, 512; 524/100, 102

(56) References Cited

U.S. PATENT DOCUMENTS

| | | | |
|---|---|---|---|
| 4,480,092 A | 10/1984 | Lai et al. | 544/113 |
| 4,547,538 A | * 10/1985 | Lai et al. | 524/100 |
| 4,629,752 A | 12/1986 | Layer et al. | 524/100 |

FOREIGN PATENT DOCUMENTS

| | | |
|---|---|---|
| DE | 19903870 | 8/1999 |
| EP | 0299426 | 1/1989 |
| EP | 0447973 | 9/1991 |
| JP | 64-37553 | * 2/1989 |
| WO | WO 88/08863 | * 11/1988 |

* cited by examiner

*Primary Examiner*—Janet Baxter
*Assistant Examiner*—Sin J. Lee
(74) *Attorney, Agent, or Firm*—David R. Crichton

(57) ABSTRACT

A compound of formula (I) wherein n is e.g. a number from 2 to 50; $R_5'$ and $R_5''$ are e.g. a group of formula (II); $G_1$, $G_2$, $G_3$ and $G_4$ are e.g. $C_1$–$C_4$alkyl; $R_1$ is e.g. hydrogen or $C_1$–$C_4$alkyl; $R_2$ is e.g. methylene; $R_3'$ is e.g. hydrogen and $R_3''$ is e.g. hydrogen or $C_1$–$C_4$alkyl; $R_4$ is e.g. $C_2$–$C_8$alkylene; and X is e.g. —N($R_7$)$R_8$ with $R_7$ and $R_8$ being independently of one another hydrogen or $C_1$–$C_8$alkyl, is useful for stabilizing an organic material against degradation induced by light, heat or oxidation.

22 Claims, No Drawings

PIPERAZINONE DERIVATIVES

This invention relates to piperazinone derivatives, to an organic material susceptible to light, heat or oxidation, containing a piperazinone derivative and to a method for stabilizing such an organic material. This invention further relates to intermediate products.

Several piperazinone derivatives and their use as stabilizers are described in U.S. Pat. Nos. 4,629,752 and 4,480,092.

The present invention relates in particular to a compound of the formula (I)

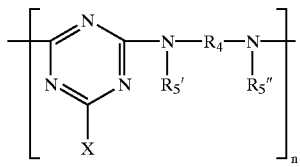
(I)

wherein
at least one group of the formula (II)

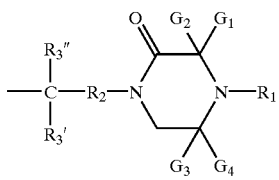
(II)

is present in the repeating unit of the formula (I);

n is a number from 1 to 100;

$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$R_1$ is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

$R_2$ is $C_2$–$C_{14}$alkylene or a group —CR$_2$'(R$_2$")— with $R_2$' and $R_2$" being independently of one another hydrogen, $C_1$–$C_{18}$alkyl or $C_5$–$C_{12}$cycloalkyl;

$R_3$' and $R_3$" are independently of one another hydrogen, $C_1$–$C_{18}$alkyl, $C_2$–$C_{18}$alkyl interrupted by oxygen; or $C_5$–$C_{12}$cycloalkyl;

$R_4$ is $C_2$–$C_{14}$alkylene, $C_4$–$C_{14}$alkylene interrupted by oxygen or sulphur; $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

$R_5$' and $R_5$" are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II) or $C_2$–$C_4$alkyl which is substituted in the 2, 3 or 4 position by —OH, $C_1$–$C_8$alkoxy, di($C_1$–$C_4$alkyl)amino or a group of the formula (III);

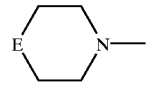
(III)

with E being a direct bond, —O—, —CH$_2$—, —CH$_2$CH$_2$— or >N—CH$_3$;

X is —OR$_6$, —SR$_6$, —N(R$_7$)(R$_8$) or a group of the formula (IV);

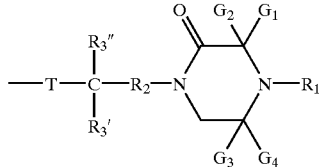
(IV)

$R_6$ $R_7$ and $R_8$ are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_{12}$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_8$alkoxy, di($C_1$–$C_4$alkyl)amino or a group of the formula (III);

or —N(R$_7$)(R$_8$) is additionally a group of the formula (III);

T is —O— or >N—R$_9$; and $R_9$ is hydrogen, $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2,or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by $C_1$–$C_8$alkoxy, di($C_1$–$C_4$alkyl)amino or a group of the formula (III);

the radicals $R_1$, the radicals $R_2$, the radicals $R_3$', the radicals $R_3$", the radicals $G_1$, the radicals $G_2$, the radicals $G_3$ or the radicals $G_4$, independently of one another, have the same or a different meaning; and in the individual recurrent units of the formula (I), each of the radicals X, $R_4$, $R_5$' and $R_5$" has the same or a different meaning;

with the proviso that one of the radicals $R_5$' and $R_5$" is different from hydrogen, when X is a group of the formula (IV) with T being >N—R$_9$.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$G_1$, $G_2$, $G_3$ and $G_4$ are preferably $C_1$–$C_4$alkyl, in particular methyl.

One of the preferred meanings of $R_1$ is $C_1$–$C_4$alkyl, in particular methyl.

One of the preferred meanings of $R_3'$ and $R_3''$ are $C_1$–$C_8$alkyl, in particular $C_1$–$C_4$alkyl, for example methyl.

One of the preferred meanings of $R_7$, $R_8$ and $R_9$ is $C_1$–$C_8$alkyl.

An example of $C_2$–$C_{18}$hydroxyalkyl and of $C_2$–$C_4$alkyl substituted by —OH is 2-hydroxyethyl.

Examples of $C_2$–$C_{18}$alkyl interrupted by oxygen and of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

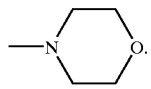

Preferred examples of $C_2$–$C_4$alkyl substituted by a group of the formula (III) are groups of the formula

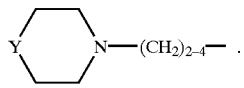

The group

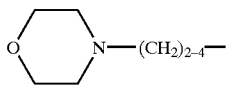

is particularly preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

An example of $C_3$–$C_8$alkynyl is 2-butynyl.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy and octoxy, is one of the preferred meanings of $R_1$.

Examples of acyl (aliphatic, cycloaliphatic or aromatic) containing not more than 8 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of $C_1$–$C_{18}$alkanoyloxy are formyloxy, acetyloxy, propionyloxy, butyryloxy, pentanoyloxy, hexanoyloxy, heptanoyloxy and octanoyloxy.

Examples of ($C_1$–$C_{18}$alkoxy)carbonyl are methoxycarbonyl, ethoxycarbonyl, propoxycarbonyl, butoxycarbonyl, pentyloxycarbonyl, hexyloxycarbonyl, heptyloxycarbonyl and octyloxycarbonyl.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted $C_5$–$C_8$cycloalkyl, in particular cyclohexyl, is preferred.

Examples of $C_5$–$C_{12}$cycloalkoxy are cyclopentoxy, cyclohexoxy, cycloheptoxy, cyclooctoxy, cyclodecyloxy, cyclododecyloxy and methylcyclohexoxy. $C_5$–$C_8$Cycloalkoxy, in particular cyclopentoxy and cyclohexoxy, is preferred.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_{12}$phenylalkyl which is unsubstituted or substituted on the phenyl by 1, 2 or 3 $C_1$–$C_4$alkyl or $C_1$–$C_4$alkoxy are benzyl, methylbenzyl, dimethylbenzyl, trimethylbenzyl, t-butylbenzyl, 2-phenylethyl and methoxybenzyl. $C_7$–$C_9$phenylalkyl, in particular benzyl, is preferred.

Example of $C_7$–$C_{12}$phenylalkoxy unsubstituted or substituted on the phenyl by 1, 2 or 3 $C_1$–$C_4$alkyl or $C_1$–$C_4$alkoxy are benzyloxy, methylbenzyloxy, dimethylbenzyloxy, trimethylbenzyloxy, t-butylbenzyloxy, 2-phenylethyloxy and methoxybenzyloxy. $C_7$–$C_9$phenylalkoxyl, in particular benzyloxy, is preferred.

Examples of alkylene containing not more than 14 carbon atoms are ethylene, propylene, trimethylene, tetramethylene, pentamethylene, hexamethylene, octamethylene, decamethylene and dodecamethylene. $R_4$ is for example $C_2$–$C_8$alkylene, preferably hexamethylene.

$R_2$ as a group —$CR_2'(R_2'')$— is preferably methylene.

Examples of $C_4$–$C_{14}$alkylene interrupted by —O— or —S—, e.g. 1, 2 or 3 —O— or —S—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl, 4,7,10-trioxatridecane-1,13-diyl, 3-thiapentane-1,5-diyl, 4-thiaheptane-1,7-diyl, 3,6-dithiaoctane-1,8-diyl, 4,7-dithiadecane-1,10-diyl, 4,9-dithiadodecane-1,12-diyl, 3,6,9-trithiaundecane-1,11-diyl and 4,7,10-trithiatridecane-1,13-diyl.

An example of $C_5$–$C_7$cycloalkylene is cyclohexylene.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

n is for example a number from 1 to 100, 2 to 100, 3 to 100, 4 to 100, 5 to 100, 6 to 100, 1 to 50, 2 to 50, 3 to 50, 4 to 50, 5 to 50, 6 to 50, 1 to 30, 2 to 30, 3 to 30, 4 to 30, 5 to 30, 6 to 30, 1 to 20, 2 to 20, 3 to 20, 4 to 20, 5 to 20 or 6 to 20. n as a number from 2 to 50, in particular 3 to 7, is preferred.

$R_5'$ and $R_5''$ are preferably a group of the formula (II).

$R_3'$ is preferably hydrogen.

$R_2$ is preferably methylene.

X is preferably a group —$N(R_7)(R_8)$, in particular —NH($R_8$).

$R_1$ is preferably hydrogen, $C_1$–$C_4$alkyl, —OH, allyl, $C_1$–$C_{12}$alkoxy, $C_5$–$C_8$cycloalkoxy, benzyl or acetyl, in particular hydrogen or $C_1$–$C_4$alkyl such as methyl.

Preferred compounds of the formula (I) are those wherein
  $G_1$, $G_2$, $G_3$ and $G_4$ are independently of one another $C_1$–$C_6$alkyl or cyclohexyl or the radicals $G_1$ and $G_2$ and the radicals $G_3$ and $G_4$ form independently of one another, together with the carbon atom they are attached to, cyclohexyl;

R$_2$ is C$_2$–C$_8$alkylene or a group —CR$_2$'(R$_2$")— with R$_2$' and R$_2$" being independently of one another hydrogen, C$_1$–C$_8$alkyl or C$_5$–C$_8$cycloalkyl;

R$_3$' and R$_3$" are independently of one another hydrogen, C$_1$–C$_8$alkyl, C$_2$–C$_8$alkyl interrupted by oxygen; or C$_5$–C$_8$cycloalkyl;

R$_4$ is C$_2$–C$_{10}$alkylene, C$_4$–C$_{10}$alkylene interrupted by oxygen or sulphur; cyclohexylene, cyclohexylenedi(C$_1$–C$_4$alkylene), C$_1$–C$_4$alkylenedi(cyclohexylene) or phenylenedi(C$_1$–C$_4$alkylene);

R$_5$' and R$_5$" are independently of one another hydrogen, C$_1$–C$_8$alkyl, C$_3$–C$_{12}$alkenyl, C$_5$–C$_8$cycloalkyl which is unsubstituted or substituted by 1, 2 or 3 C$_1$–C$_4$alkyl; C$_7$–C$_9$phenylalkyl; tetrahydrofurfuryl, a group of the formula (II) or C$_2$–C$_4$alkyl which is substituted in the 2, 3 or 4 position by —OH, C$_1$–C$_4$alkoxy, di(C$_1$–C$_4$alkyl)amino or a group of the formula (III);

R$_6$, R$_7$ and R$_8$ are independently of one another hydrogen, C$_1$–C$_8$alkyl, C$_3$–C$_{12}$alkenyl, C$_5$–C$_8$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$C$_4$alkoxy; C$_7$–C$_{12}$phenylalkyl; tetrahydrofurfuryl or C$_2$–C$_4$alkyl which is substituted in the 2, 3 or 4 position by C$_1$–C$_4$alkoxy, di(C$_1$–C$_4$alkyl)amino or a group of the formula (III);

or —N(R$_7$)(R$_8$) is additionally a group of the formula (III); and

R$_9$ is hydrogen, C$_1$–C$_8$alkyl, C$_2$–C$_8$hydroxyalkyl, C$_3$–C$_{12}$alkenyl, C$_5$–C$_8$cycloalkyl which is unsubstituted or substituted by 1, 2 or 3 C$_1$–C$_4$alkyl; C$_7$–C$_{12}$phenylalkyl; tetrahydrofurfuryl, a group of the formula (II), or C$_2$–C$_4$alkyl which is substituted in the 2, 3 or 4 position by C$_1$–C$_4$alkoxy, di(C$_1$–C$_4$alkyl)amino or a group of the formula (III).

Particularly preferred compounds of the formula (I) are those wherein

G$_1$, G$_2$, G$_3$ and G$_4$ are independently of one another C$_1$–C$_4$alkyl;

R$_2$ is C$_2$–C$_4$alkylene or a group —CR$_2$'(R$_2$")— with R$_2$' and R$_2$" being independently of one another hydrogen or C$_1$–C$_4$alkyl;

R$_3$' and R$_3$" are independently of one another hydrogen or C$_1$–C$_4$alkyl;

R$_4$ is C$_2$–C$_{10}$alkylene;

R$_5$' and R$_5$" are independently of one another hydrogen, C$_1$–C$_4$alkyl, C$_3$–C$_8$alkenyl, cyclohexyl, benzyl or a group of the formula (II);

X is —N(R$_7$)(R$_8$) or a group of the formula (IV);

R$_7$ and R$_8$ are independently of one another hydrogen or C$_1$–C$_8$alkyl;

or —N(R$_7$)(R$_8$) is additionally a group of the formula (III) with E being —O—; and R$_9$ is hydrogen, C$_1$–C$_8$alkyl or cyclohexyl.

Compounds of the formula (I) which are of particular interest are those wherein n is a number from 2 to 50;

G$_1$, G$_2$, G$_3$ and G$_4$ are independently of one another C$_1$–C$_4$alkyl;

R$_1$ is hydrogen or C$_1$–C$_4$alkyl;

R$_2$ is methylene;

R$_3$' is hydrogen and R$_3$" is hydrogen or C$_1$–C$_4$alkyl;

R$_4$ is C$_2$–C$_8$alkylene;

R$_5$' and R$_5$" are a group of the formula (II); and

X is —N(R$_7$)(R$_8$) with R$_7$ and R$_8$ being independently of one another hydrogen or C$_1$–C$_8$alkyl.

The definition of the terminal groups which saturate the free valences in the compounds of the formula (I) depends on the process used for their preparation. The terminal groups can also be modified after the preparation of these compounds.

The compounds of the formula (I) may be prepared, for example, by reacting a compound of the formula (Z-00)

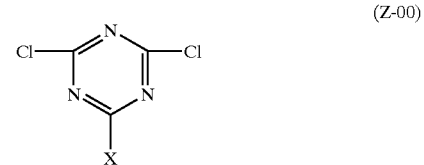

(Z-00)

with a compound of the formula (Z-0)

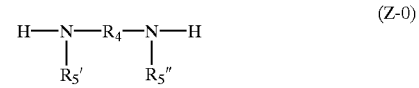

(Z-0)

wherein X, R$_4$, R$_5$' and R$_5$" are as defined above. Either the compound of the formula (Z-00) or the compound of the formula (Z-0) can be used in an excess of up to 20 mol %, preferably 5 mol %. The molar ratio of the compounds of the formulae (Z-00) and (Z-0) is in particular 1:1.1. According to a preferred procedure, the compound of the formula (Z-0) is used in an excess of up to 5 mol %.

The reaction is preferably carried out in an inert organic solvent, for example toluene, xylene or benzene, in the presence of an inorganic base at a temperature of 40° to 145° C., in particular 60° to 140° C. Examples of a base are NaOH, KOH, Na$_2$CO$_3$ and K$_2$CO$_3$.

In this case, the terminal group bonded to the diamino radical may be hydrogen or a group

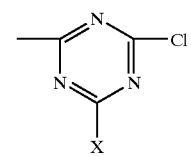

and the terminal group bonded to the triazine radical may be Cl or a group

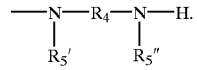

When the terminal group is Cl, it is advantageous to replace it, for example, by a group —X as defined above, in particular —OH, an amino group —N(R$_7$)(R$_8$) or a group of the formula (IV), after the reaction is complete. Examples of suitable replacement groups are pyrrolidin-1-yl, morpholino, —NH$_2$, —N(C$_1$–C$_8$alkyl)$_2$ and —NR(C$_1$–C$_8$alkyl) with R being hydrogen or a group of the formula (II).

It is further advantageous to replace the terminal hydrogen of the group

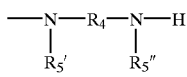

by $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$.

$C_1$–$C_8$acyl, preferably $C_1$–$C_8$alkanoyl, in particular acetyl as shown below in EXAMPLE 5 is preferred.

A preferred embodiment of this invention relates to compounds of the formula (I) wherein the terminal group attached to the diamino radical is hydrogen, $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$, and the terminal group attached to the triazine residue is a group

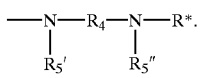

with R' being hydrogen, $C_1$–$C_8$acyl, ($C_1$–$C_8$alkoxy)carbonyl, ($C_5$–$C_{12}$cycloalkoxy)carbonyl, ($C_1$–$C_8$alkyl)aminocarbonyl, ($C_5$–$C_{12}$cycloalkyl)aminocarbonyl, ($C_7$–$C_9$phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$.

A particularly preferred embodiment of this invention relates to compounds of the formula (I) wherein the terminal group attached to the diamino radical is $C_1$–$C_8$alkanoyl and the terminal group attached to the triazine residue is a group

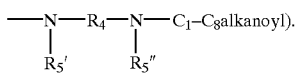

Compounds of the formula (Z-0) wherein $R_5'$ is a group of the formula (II) correspond to the formula (Z-1)

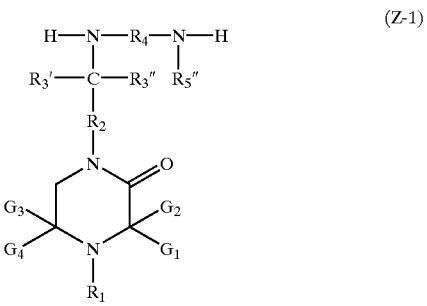

with $G_1$, $G_2$, $G_3$, $G_4$, $R_1$, $R_2$, $R_3'$, $R_3''$, $R_4$ and $R_5''$ being as defined above, and constitute a further embodiment of this invention.

When $R_3'$ and/or $R_3''$ are hydrogen, a compound of the formula (Z-1) wherein $R_5''$ is optionally a group of the formula (II) can be prepared, for example, by reacting—in a stoichiometric ratio—a ketone of the formula (Z-2)

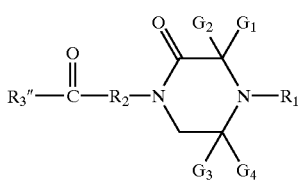

with a diamine of the formula (Z-3)

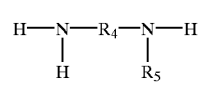

wherein $G_1$, $G_2$, $G_3$, $G_4$, $R_1$, $R_2$, $R_3''$ and $R_4$ are as defined above and $R_5$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, or $C_2$–$C_4$alkyl which is substituted in the 2, 3 or 4 position by —OH, $C_1$–$C_8$alkoxy, di($C_1$–$C_4$alkyl)amino or a group of the formula (III), and subsequent hydrogenation.

The reaction which is a reductive amination is conveniently carried out under a hydrogen pressure of 30 to 35 atm in the presence of a hydrogenation catalyst such as platinum on carbon, palladium or Raney nickel, in particular platinum on carbon, in neat or in an organic solvent, for example methanol or a mixture of isopropanol and water. The temperature is preferably 40° to 100° C.

When $R_3'$ and $R_3''$ are different from hydrogen, the compound of the formula (Z-1) may be prepared, for example, by adding an organometallic derivative of the formula $R_3'$—M with $R_3'$ being $C_1$–$C_{18}$alkyl, $C_2$–$C_{18}$alkyl interrupted by oxygen; or $C_5$–$C_{12}$cycloalkyl and M being $Li^+$, $MgCl^+$, $Na^+$, $K^+$ or $Cu^+$, in particular $Li^+$, to a solution of the corresponding ketimine in an inert organic solvent such as diethyl ether, tetrahydrofurane or xylene at low temperature, for example −78°–0° C. The reaction may be carried out in analogy to the procedure described in "Advanced Organic Chemistry, Jerry March, John Wiley & Sons, 4 th edition, pp 934–935" or in "The chemistry of the carbon-nitrogen double bond, edited by S. Patai, John Wiley & Sons, 1970, pp 266–272".

The ketone of the formula (Z-2) which constitute a further embodiment of this invention can be prepared, for example, by oxidation of a compound of the formula (Z-4)

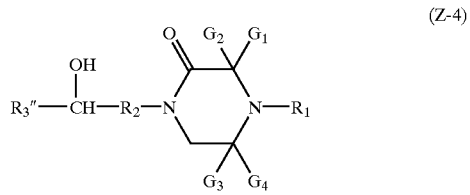

wherein $G_1$, $G_2$, $G_3$, $G_4$, $R_1$, $R_2$ and $R_3''$ are as defined above. The reaction may be carried out analogously to the Swern oxidation (Fieser and Fieser's Reagents for Organic Synthesis, Volume 8, John Wiley & Sons, 1980, page 200).

The compounds of the formula (Z-4) can be prepared, for example, in analogy to the method described in U.S. Pat. No. 4,167,512.

The compounds of the formula (I) as well as the intermediates of the formulae (Z-1) and (Z-2) are very effective in improving the light, heat and oxidation resistance of organic materials, especially synthetic polymers and copolymers.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
   a) radical polymerisation (normally under high pressure and at elevated temperature).
   b) catalytic polymerisation using a catalyst that normally contains one or more than one metal of groups IVb, Vb, VIb or VIIU of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadieneistyrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/ alkoxyalkyl acrylate or acrylonitrile/vinyl halide copolymers or acrylonitrile/alkyl methacrylate/ butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/ formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PANHDPE, PA/PP, PA/PPO, PBT/PC/ ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixturesbof synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/ butadiene copolymers.

This invention thus also relates to a composition comprising an organic material susceptible to degradation induced by light, heat or oxidation and at least one compound of the formula (I).

The organic material is preferably a synthetic polymer, more particularly one selected from the aforementioned groups.

A thermoplastic rubber (TPR) as an organic material is also of interest.

Polyolefins and their copolymers, for example those listed above under items 1–3, in particular polyethylene and polypropylene, are preferred.

Polycarbonate such as in item 19 above, and blends, such as in item 28 above, thermoplastic polyurethan (TPU) or polyacetal are also preferred.

Other materials which may be stabilized with the compounds of the formula (I) are recording materials for photographic reproduction and other reprographic techniques as described for example in Research Disclosure 1990, 31429 (pages 474–480), GB-A-2,319,523 or DE-A-19,750,906, page 22, line 15 to page 105, line 32.

Thus, a further embodiment of this invention is a recording material, in particular a photographic material, containing at least one compound of the formula (I).

Of special importance is also the stabilization of non-silver reprographic materials, for example, those used for pressure-sensitive copying systems, microcapsule photocopier systems, heat-sensitive copier systems and ink-jet printing.

The recording materials stabilized with the compounds of the formula (I) have an unexpectedly high quality, especially in terms of their light stability.

The recording materials have a structure which is known per se and which corresponds to their utility. They consist of a base, for example a paper or plastic film, on which one or more coatings are applied. Depending on the type of the material, these coats contain the suitable components required. In the case of photographic materials, the coats contain for example silver halide emulsions, colour couplers, dyes and the like. The material intended for ink-jet printing has e.g. a customary base on which an absorption layer suitable for ink is located. Uncoated paper can likewise be employed for ink-jet printing. In the latter case, the paper simultaneously functions as a base and has the absorbent for the ink. Suitable materials for ink-jet printing are described, inter alia, in U.S. Pat. No. 5,073,448, the disclosure content of which is regarded as part of the present description.

The recording material can also be transparent, for example in the case of projection films.

The compound of the formula (I) can be incorporated into the material even in the course of manufacture; in papermaking, for example, by addition to the pulp. Another method of use is the spraying of the material with an aqueous solution of the compound of the formula (I), or the addition thereof to the coating.

Coatings for transparent recording materials for projection must not contain any light-scattering particles such as pigments or fillers.

The colour-binding coatings can contain further additives, for example antioxidants, light stabilizers (including UV absorbers and/or conventional hindered amine light stabilizers), viscosity improvers, brighteners, biocides and/or antistats.

The coating is usually prepared as described in the following. The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula (I) is that they can easily be incorporated into the coating.

As mentioned above, the recording materials cover a broad field of use. Compounds of the formula (I) can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966, 4,483,912, 4,352,200, 4,535,050, 4,536,463, 4,551,407, 4,562,137 and 4,608,330 and also in EP-A-139,479, EP-A-162,664, EP-A-164,931, EP-A-237, 024, EP-A-237,025 and EP-A-260,129. In all these systems, the compounds of the formula (I) can be added to the colour-accepting layer. Alternatively, the compounds of the formula (I) can be added to the donor layer for protecting the colour formers against light.

The compounds of the formula (I) can also be employed in recording materials which are based on the principle of photopolymerization, photosoftening or the rupture of microcapsules, or, when heat-sensitive or photosensitive diazonium salts, leuco dyes with oxidizing agent or colour iactones with Lewis acids are used.

Heat-sensitive recording material exploits the colour-imparting reaction between a colourless or weakly coloured base dye and an organic or inorganic colour developer; the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula (I). If a protective layer is present, the compound of the formula (I) can also be incorporated into the protective layer.

Heat-sensitive recording materials are described, for example, in JP-A-Hei 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing as described for example in EP-A-507,734.

Compounds of the formula (I) can also be employed in inks (preferably for inkjet printing) for example as described in U.S. Pat. No. 5,098,477, the disclosure content of which is regarded as part of the present description. The invention therefore preferably also relates to an ink comprising at least one compound of the formula (I) as stabilizer. The ink, especially for ink-jet printing, contains preferably water. Inks contain the stabilizer of the formula (I) usually in a concentration of from 0.01 to 20% by weight, in particular from 0.5 to 10% by weight.

The photographic material according to this invention can be a black and white or can be a colour photographic material. A colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

Details of the photographic materials to be stabilized according to this invention and components which can be employed therein are given, inter alia, in GB-A-2,319,523, DE-A-19,750,906, page 23, line 20 to page 105, line 32, and U.S. Pat. No. 5,538,840, column 25, line 60 to column 106, line 31. These parts of U.S. Pat. No. 5,538,840 are incorporated herein by way of reference.

The compounds of this invention can be introduced in any layer of a silver halide photographic material, however, they are preferably incorporated in a chromogenic layer, in particular in a layer containing a yellow coupler. They are used, for example, in a 1% to 200% weight ratio with the coupler, preferably 1% to 100%. The compounds of the present invention can be used in combination with other conventional stabilizers that can be incorporated in the same layer or in a different layer. Examples of suitable conventional stabilizers are described in GB-A-2,319,523, DE-A-19,750,906 and U.S. Pat. No. 5,538,840 and include in particular phenolic stabilizers, conventional hindered amine stabilzers, UV absorbers, preferably those of the hydroxyphenyl benztriazole type or of the hydroxyphenyl triazine class, and the like.

Examples of yellow couplers are also disclosed in U.S. Pat. No. 5,538,840, column 33, line 3 to column 47, line 15.

Thus, further preferred embodiments of this invention are:

(1) A photographic material comprising on a substrate at least one layer containing a compound of the formula (I).

(2) A silver halide colour photographic material comprising a support having thereon at least one light-sensitive silver halide emulsion layer and optionally a non-light sensitive emulsion layer, characterized in that at least one light-sensitive layer contains a compound of the formula (I).

(3) A silver halide colour photographic material comprising a support having thereon
   a) at least one cyan-forming unit composed of a red-sensitive silver halide emulsion layer containing a cyan dye-forming coupler,
   b) at least one magenta-forming unit composed of a green-sensitive silver halide emulsion layer containing a magenta dye-forming coupler and
   c) at least one yellow-forming unit composed of a blue-sensitive silver halide emulsion layer containing a yellow dye-forming coupler, characterized in that the blue-sensitive layer contains a compound of the formula (I).

A further embodiment of this invention is a method for stabilizing an organic material against degradation induced by light, heat or oxidation, which comprises incorporating into said organic material at least one compound of the formula (I).

The compounds of the formula (I) can be used in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably 0.05 to 2%, in particular 0.05 to 1%.

The compounds of the formula (I) can be added, for example, to the polymeric materials before, during or after the polymerization or crosslinking of the said materials. Furthermore, they can be incorporated in the polymeric materials in the pure form or encapsulated in waxes, oils or polymers.

In general, the compounds of the formula (I) can be incorporated in the polymeric materials by various processes, such as dry mixing in the form of powder, or wet mixing in the form of solutions or suspensions or also in the form of a masterbatch which contains the compounds of the formula (I) in a concentration of 2.5 to 25% by weight; in such operations, the polymer can be used in the form of powder, granules, solutions, suspensions or in the form of latices.

The materials stabilized with the compounds of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of the formula (I).

Particular examples of said conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenot, 2,6-dicyclopentyl-4-methylphenol, 2-(a-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl- 4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3.5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugardo®XL-1 supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl/diphenylamines, a mixture of mono- und dialkylated tert-butyidiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethyipiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl- 2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'hydroxyphenyl) benzotriazole, 2-(3'-dodecyl-2'-hydroxy-5'-methylphenyl) benzotriazole, 2-(3'-tert-butyl-2'-hydroxy5'-(2-isooctyloxycarbonylethyl)phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]— where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate-isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-βcyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of, 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)-4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N,'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2- hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butytphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-1 2-methyl-dibenz[d,g]-1,3,2-dioxaphosphocin, bis(2,4-di-tert-butyl-6-methylphenyl) methyl phosphite, bis(2,4-di-tertbutyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3', 5,5'-tetra-tert-butyl-1,1'-biphenyl-2,2'-di-yl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-7one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the compounds of the formula (I) to the conventional additives may be for example 1:0.5 to 1:5.

This invention is illustrated in more detail by the following Examples. All percentages are by weight, unless otherwise indicated. The compounds disclosed in Examples 1A), 1B), 1C), 4A) and 4B) relate to a particular preferred embodiment of the present invention.

EXAMPLE 1

A) Preparation of the Intermediate of the Formula

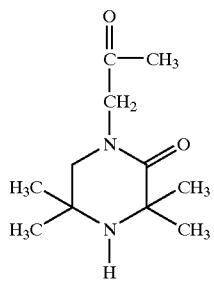

1) Preparation of 1-(2-nitro-2-methylpropylamino)propan-2-ol

Following the procedure described below in EXAMPLE 4A, step 1, 526.3 g (6.66 mol) of 1-amino-2-propanol (95%) are reacted with 561.6 g (6.05 mol) of 2-nitropropane (96%) and 181.7 g (6.05 mol) of paraformaldehyde in 100 ml of isopropanol to give the product which is used in the following reaction without any isolation.

2) Preparation of 1-(?-amino-2-methylpropylamino)propan-2-ol

Following the procedure described below in EXAMPLE 4A, step 2, the mixture of above step 1 is hydrogenated by using 100 g of Raney Ni as a catalyst. A white oil with a boiling point of 116°–120° C. at 13.3 mbar is obtained.

3) Preparation of 1-(2-hydroxypropyl)-3,3,5,5-tetramethylpiperazin-2-one

Following the procedure described below in EXAMPLE 4A, step 3, 250 g (1.71 mol) of 1-(2-amino-2-methylpropylamino)propan-2-ol are reacted with 306.2 g (2.57 mol) of chloroform and 1509 ml of acetone in the presence of 410.4 g (10.26 mol) of sodium hydroxide in 410 ml of water. A yellow oil with a boiling point of 137°–140° C. at 1.1 mbar is obtained.

4) The intermediate of the above formula is prepared by adding 107 g (0.5 mol) of dimethylsulfoxide drop by drop to a solution of 63.5 g (0.5 mol) of oxalyl chloride in 800 ml of dichloromethane cooled to −60° C. After the addition, a solution of 1-(2-hydroxypropyl)-3,3,5,5-tetramethylpiperazin-2-one in 300 ml of dichloromethane are slowly added, keeping the temperature at −60° C. After 20 minutes, 101 g (1 mol) of triethylamine are added. After additional 30 minutes, the temperature is increased to room temperature. Then, the mixture is filtered and evaporated under vacuum. The row material is purified by distillation (129° C./1 mmHg). The product is recovered as a yellow oil. The yield is 80% of theory.

$^1$H NMR: 4.03 (s, 2H); 3.11 (s, 2H); 2.018 (s, 3H); 1.24 (s, 6H); 1.09 (s, 6H)

B) Preparation of the Intermediate of the Formula

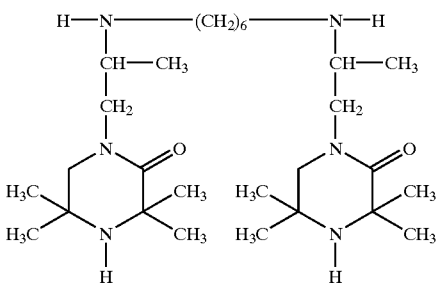

At room temperature, 50 g of Pt (5%) supported on carbon with 50% water are added to a mixture of 132.4 g (0.62 mol) of 3,3,5,5-tetramethyl-1-(2-oxopropyl)piperazin-2-one and 36.2 g (0.31 mol) of hexamethylendiamine in methanol. The mixture is hydrogenated at 70° C. and 35 bar for 20 hours. Then, the mixture is filtered and the organic phase is washed with water, dehydrated on sodium sulphate and evaporated under vacuum. The product is recovered as a yellow resin. The yield is 93% of theory.

$^1$H NMR: 3.37 (dd, 2H); 3.17 (s, 4H); 3.14 (dd, 2H); 2.82 (sext, 2H); 2.61–2.40 (m, 4H); 1.33 (m, 4H); 1.27 (s, 12H); 1.22 (s, 4H); 1.10 (s, 12H); 0.96 (d, 6H)

C) Preparation of the Compound of the Formula

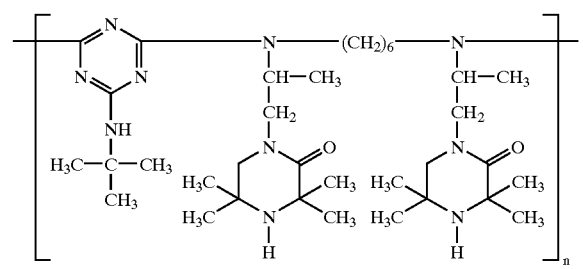

46.5 g (0.21 mol) of 2-tert-butylamino-4,6-dichlorotriazine in 500 ml of xylene are added to a solution of 125 g (0.23 mol) of the intermediate described under B) in 300 ml of xylene. The solution is heated at 60° C. for 2 hours, under stirring. Then, 25.2 g (0.63 mol) of NaOH in 50 ml of water are added. The mixture is heated to reflux for 5 hours, the water being removed by azeotropic distillation. Subsequently, the mixture is cooled to 60° C. and 29 g (0.21 mol) of sodium carbonate in 50 ml of water are added and the mixture is refluxed for additional 24 hours, the water being removed by azeotropic distillation. Then, the mixture is cooled and filtered. The organic phase is dehydrated on sodium sulphate and evaporated under vacuum. 153.3 g of the product are recovered. The yield is 98% of theory.

Melting point: 96°–99° C.

EXAMPLE 2
Preparation of the Compound of the Formula

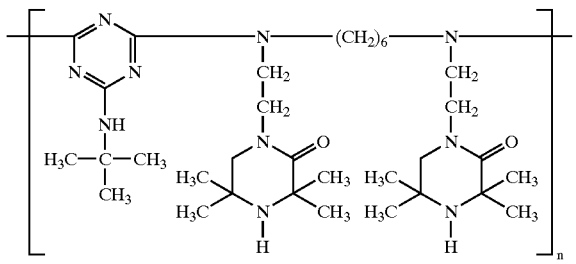

The compound is prepared in analogy to the method described in EXAMPLE 1, using the appropriate starting materials.

Melting point: 130°–140° C. (yellow powder)

EXAMPLE 3
Preparation of the Compound of the Formula

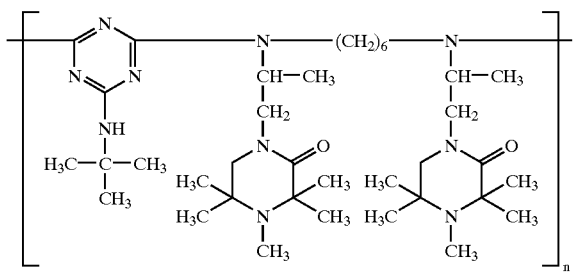

5 g of paraformaldehyde are added to a solution of 36.1 g (0.055 mol) of the compound of EXAMPLE 1C in tert-amyl alcohol. The mixture is heated to 80° C. and 7.6 g (0.165 mol) of formic acid dissolved in 10 ml of tert-amyl alcohol are slowly added. The mixture is then stirred for 3 hours at 80° C. Then, 50 ml of toluene are added, the temperature being cooled down to room temperature. Subsequently, a solution of 6.6 g (0.165 mol) of sodium hydroxide in 50 ml of water is slowly added. After stirring for ½ hour, the organic phase is separated, washed twice with water, dried over anhydrous sodium sulfate, filtered and evaporated under vacuum (80° C./1.3 mbar).

Melting point: 95°–99° C.

EXAMPLE 4
A) Preparation of the Intermediate of the Formula

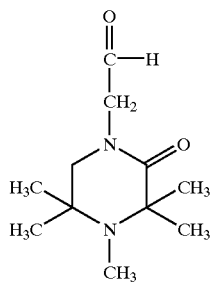

1) Preparation of 2-(2-nitro-2-methyl-propylamino)ethanol 607.8 g (6.55 mol) of 2-nitropropane and 100 ml of water are added to a solution of 450 g (7.40 mol) of ethanolamine in 1000 ml of isopropanol. The solution is stirred at room temperature and 225.4 g (7.5 mol) of paraformaldehyde and 7 ml of 20% aqueous solution of sodium hydroxide (% w/v) are added under stirring and maintaining the temperature at room temperature for 16 hours. The mixture is then heated to 50° C. with nitrogen being bubbled into the mixture to eliminate the formaldehyde in excess. The mixture obtained is used for the following reaction without any isolation of the product.

2) Preparation of 2-(2-amino-2-methyl-propylamino)ethanol

The mixture of 1) is transferred into an autoclave and 100 g of Raney Ni are added. The autoclave is closed and purged with nitrogen. Hydrogen is added until the pressure is 50 bars. The mixture is maintained under a hydrogen pressure of 50 bars at room temperature and under stirring for 8 hours. Subsequently, the mixture is heated to 50° C. at the same pressure. The catalyst is then separated off by filtration and the mixture is distilled under vacuum. A white oil with a boiling point of 100°–105° C. at 13.3 mbar is obtained.

3) Preparation of 1-(2-hydroxyethyl)-3,3,5,5-tetramethylpiperazin-2-one 244.2 g (2.05 mol) of chloroform are added to 180 g (1.36 mol) of 2-(2-amino-2-methylpropylamino)ethanol in 1204 ml of acetone. The mixture is cooled to 5° C. under stirring and a solution of 327 g (8.18 mol) of sodium hydroxide in 327 ml of water is slowly added, the temperature of the mixture being maintained at 0°–5° C. during the addition. The mixture is then stirred at this temperature for further 2 hours and at room temperature for 15 hours. Subsequently, the pH of the aqueous solution is corrected to 11 and the mixture is stirred for further 4 hours. Then, the mixture is filtered and the residue is washed with acetone. The filtrate and the acetone of washing are collected and evaporated under vacuum (70° C./24 mbar). The residue is distilled giving a white oil with a boiling point of 115° C. at 2.66 mbar. After cooling a solid product with a melting point of 91°–93° C. is obtained.

4) Preparation of 1-(2-hydroxyethyl)-3,3,4,5,5-pentamethylpiperazin-2-one 24.3 g (0.78 mol) of paraformaldehyde are added to a solution of 120 g (0.6 mol) of 1-(2-hydroxyethyl)-3,3,5,5-tetramethylpiperazin-2-one in 300 ml of tert-amyl alcohol. The mixture is then heated to 80° C. and 35.8 g (0.78 mol) of formic acid dissolved in 30 ml of tert-amyl alcohol are slowly added. Then, the mixture is maintained at 80° C. for further 1 hour and cooled to 50° C. Subsequently, 250 ml of toluene and 100 ml of water are added. The mixture is then stirred and 33 g (0.825 mol) of sodium hydroxide dissolved in 60 ml of water are slowly added. The organic phase is separated, washed with water, dried over anhydrous sodium sulfate, filtered and evaporated under vacuum (60° C./10 mbar). A white solid with a melting point of 77°–80° C. is obtained.

5) The intermediate of the above formula is prepared in analogy to the procedure described in EXAMPLE 1A, step 4, starting from 1-(2-hydroxyethyl)-3,3,4,5,5-pentamethylpiperazin-2-one. A brown oil is obtained.

$^1$H NMR: 9.50 (s, 1H); 4.06 (s, 2H); 3.07 (s, 2H); 2.20 (s, 3H); 1.27 (s, 6H); 1.06 (s, 6H)

B) Preparation of the Intermediate of the Formula

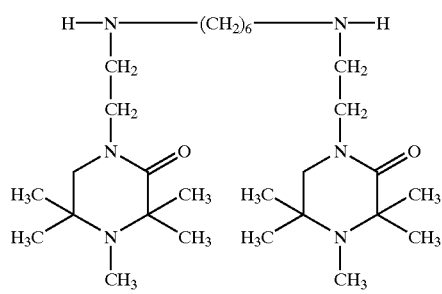

This intermediate is prepared in analogy to the procedure described in EXAMPLE 1B, starting from the intermediate of the above step A.

C) Preparation of the Compound of the Formula

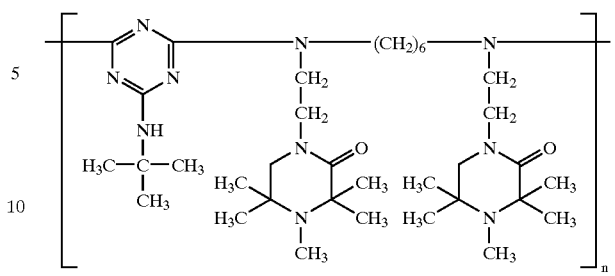

This compound is prepared in analogy to the method described in EXAMPLE 1C, using the reagent of the above step B. The product obtained is a yellow powder:

Melting point: 78°–81° C.

EXAMPLE 5

Preparation of the Compound of the Formula

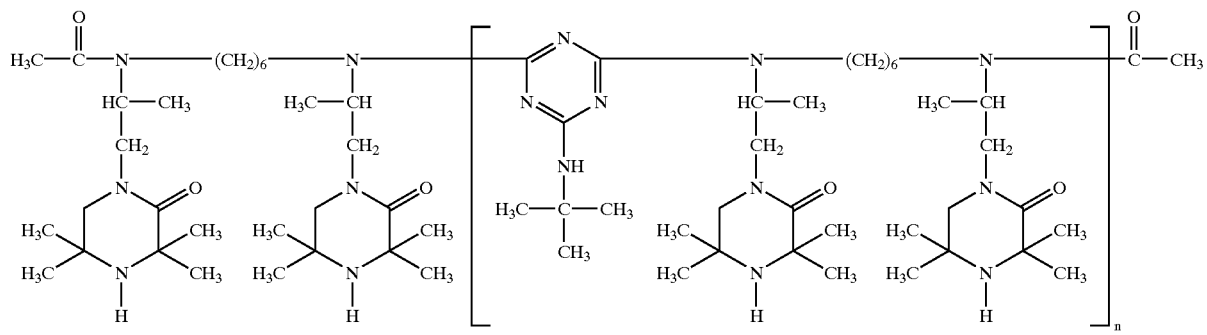

A solution of 15 g of the product of EXAMPLE 1C, 4 g (0.02 mol) of acetic anhydride and 4 g (0.02 mol) of triethylamine in 150 ml of dichloromethane is refluxed for 5 hours. After cooling, 30 ml of a 40% solution of potassium carbonate is added. The organic phase is separated, dried over anhydrous sodium sulfate, filtered and evaporated under vacuum (80° C./1.3 mbar). A white powder is obtained.

Melting point: 103°–107° C.

EXAMPLE 6

Preparation of the Compound of the Formula

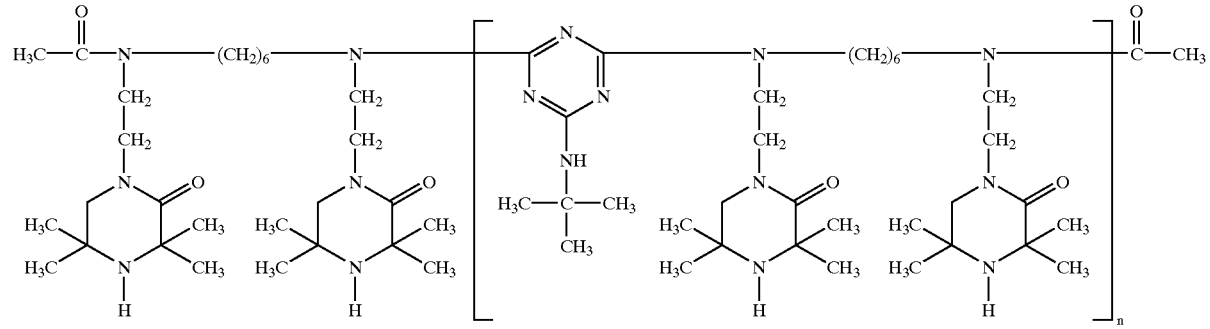

The compound is prepared in analogy to the method described in EXAMPLE 5, using the compound of EXAMPLE 2.

Melting point: 122–127° C. (yellow powder)

EXAMPLE 7
Preparation of the Compound of the Formula

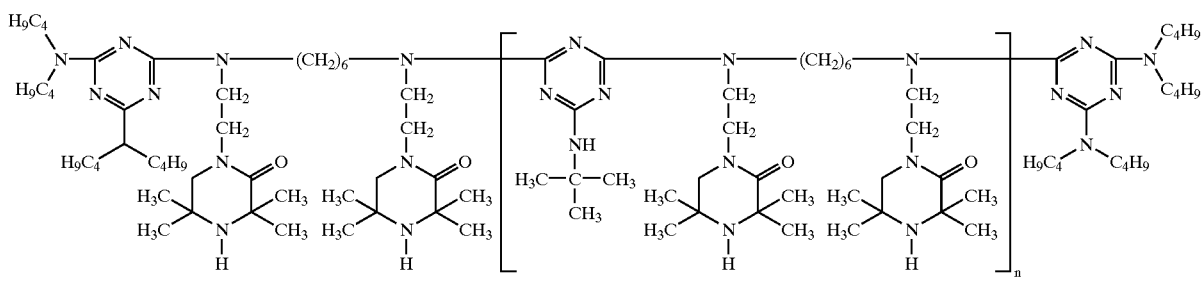

A solution of 50 g of the compound of EXAMPLE 2C and 8.9 g (0.024 mol) of 2,4-bis{dibutylamino}-6-chloro-{1,3,5}-triazine in 250 ml of xylene is allowed to react for 4 hours at 140° C. After cooling to 60° C., 0.96 g (0.024 mol) of sodium hydroxide and 4 g of potassium carbonate in 10 ml of water are added. The mixture is heated to reflux and the reaction water is azeotropically eliminated. After 6 additional hours, the mixture is cooled to 60° C., diluted with 50 ml of xylene, filtered and concentrated under vacuum at 140° C./1 mbar. A yellow powder is obtained.

Melting point: 60°–64° C.

EXAMPLE I-1

Light Stabilizing Action in Polypropylene Tapes 1 g of each of the compounds listed in Table I-1, 1 g of tris[2,4-di-tert-butylphenyl]phosphite, 0.5 g of pentaerythritol tetrakis[3-(3,5-di-tert-butyl-4-hydroxyphenyl) propionate]and 1 g of calcium stearate are mixed in a turbomixer with 1000 g of polypropylene powder (PP ®MOPLEN S SF) having a melt index of 3.7 (measured at 230° C. and 2.16 Kg).

The mixtures are extruded at 200–220° C. to give polymer granules which are subsequently converted to stretched tapes of 50 μm thickness and 2.5 mm width, using a semi-industrial type of apparatus (®Leonard-Sumirago (VA)—Italy) and working under the following conditions:

| | |
|---|---|
| Extruder temperature: | 210–230° C. |
| Head temperature: | 240–260° C. |
| Stretch ratio: | 1:6 |

The tapes thus prepared are mounted on a white card and exposed in a Weather-O-Meter 65 WR (ASTM D 2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed. The results obtained are shown in Table I-1.

TABLE I-1

| Stabilizer | $T_{50}$ (hours) |
|---|---|
| Without stabilizer | 520 |
| Compound of EXAMPLE 1C | 2620 |
| Compound of EXAMPLE 3 | 2600 |

The above results show that the compounds of this invention are effective light stabilizers.

EXAMPLE I-2

Light Stabilizing Action in Polypropylene Fibres 2.5 g of each of the compounds listed in Table I-2, 1 g of tris(2,4-di-t-butylphenyl)phosphate, 1 9 of calcium monoethyl 3,5-di-t-butyl-4-hydroxybenzyl-phosphonate, 1 g of calcium stearate and 2.5 g of titanium dioxide are mixed in a slow mixer with 1000 g of polypropylene powder (PP ®MOPLEN FLF 20) having a melt index =12.2 g/10 min (measured at 230° C. and 2.16 kg).

The mixtures are extruded at 200–230° C. to obtain polymer granules which are then converted into fibres using a pilot-type apparatus (®Leonard-Sumirago(VA), Italy) and operating under the following conditions:

| | |
|---|---|
| Extruder temperature: | 230–245° C. |
| Head temperature: | 255–260° C. |
| Draw ratio: | 1:3.5 |
| Linear density: | 11 dtex per filament |

The fibres prepared in this way are exposed, after mounting on white cardboard, in a 65WR Weather-O-Meter (ASTM D2565-85) with a black panel temperature of 63° C. For samples taken after various times of exposure to the light, the residual tenacity is measured using a constant-speed tensometer, and the exposure time in hours needed to halve the initial tenacity ($T_{50}$) is then calculated.

For purposes of comparison, fibres prepared under the same conditions as stated above, but without adding the stabilizers of the present invention, are also exposed. The results are shown in Table I-2.

TABLE I-2

| Stabilizer | $T_{50}$ (hours) |
|---|---|
| Without stabilizer | 310 |
| Compound of EXAMPLE 1C | 2790 |
| Compound of EXAMPLE 3 | 2830 |

The above results show that the compounds of this invention are effective light stabilizers.

EXAMPLE II-1
Stabilization of a Gray Pigmented Polycarbonate/acrylonitrile-butadiene-styrene (PC/ABS) Blend A commercial PC/ABS blend (®Cycoloy MC 8002) pigmented with 1% by weight of ®Gray 9779 from Uniform Color Company is stabilized by addition of 1% by weight of 2-(2'-hydroxy-3',5'-bis(1",1"-dimethylbenzyl)phenyl)benzotriazole and 0.5% by weight of the compound indicated in Table II-1. A sample containing only the 1% by weight of the benzotriazole stabilizer and an unstabilized sample—both containing 1% by weight of gray pigment—serve as comparison.

Izod bars (2.5" L×0.5" W×0.125" W) are prepared by injection molding on a ®BOY 30 machine, barrel temperature 246–268° C., die temperature 268° C. Accelerated weathering is performed using an ®Atlas Ci65A Weather-O-meter (XAW), operating in "Dry XAW" mode (ASTM G26-90, method C). After regular intervals, the color change ΔE according to DIN 6174 is determined. The results are listed in Table II-1.

TABLE II-1

| Irradiation time:<br>Stabilizer | 249.8 hours<br>ΔE | 750 hours<br>ΔE |
|---|---|---|
| None | 3.3 | 9.0 |
| Benzotriazole stabilizer*) | 1.7 | 6.7 |
| Compound of EXAMPLE 5 | 0.7 | 4.8 |

*)2-(2'-hydroxy-3',5'-bis(1",1"-dimethylbenzyl)phenyl)benzotriazole

The PC/ABS samples stabilized according to this invention show an excellent color stability.

EXAMPLE II-2
Stabilization of a White Pigmented Polycarbonate/acrylonitrile-butadiene-styrene (PC/ABS) Blend Samples are prepared from a commercial PC/ABS blend (®Cycoloy MC 8002) as described in EXAMPLE II-1 except that $TiO_2$ (®Tiona RCL-4 rutile; ®SCM chemicals) is used as pigment. Weathering and assessment is carried out as described in EXAMPLE II-1. The results are shown in Table II-2.

TABLE II-2

| Irradiation time:<br>Stabilizer | 249.6 hours<br>ΔE | 749.3 hours<br>ΔE | 999.8 hours<br>ΔE |
|---|---|---|---|
| None | 4.6 | 15.4 | 21.8 |
| Benzotriazole stabilizer*) | 2.8 | 9.5 | 15.7 |
| Compound of EXAMPLE 5 | 3.4 | 6.4 | 11.3 |

*)2-(2'-hydroxy-3',5'-bis(1",1"-dimethylbenzyl)phenyl)benzotriazole

The PC/ABS samples stabilized according to this invention show an excellent color stability, particularly at prolonged exposure intervals.

Abbreviations used in the Following EXAMPLES III-1 to III-5

CoupY1: Compound of the formula

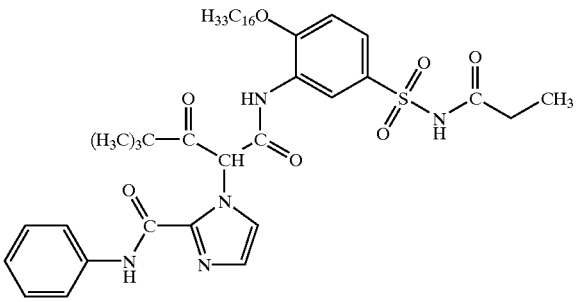

CoupY2: Compound of the formula

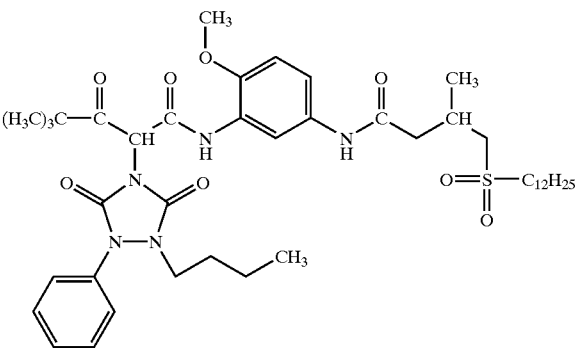

Solv1: Compound of the formula

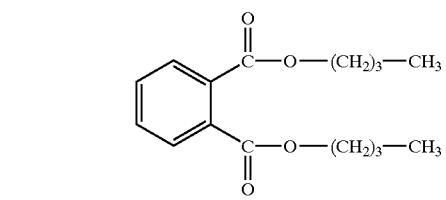

Ha1: Compound of the formula

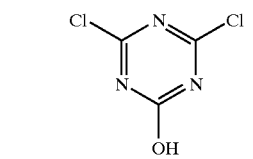

Su1: Compound of the formula

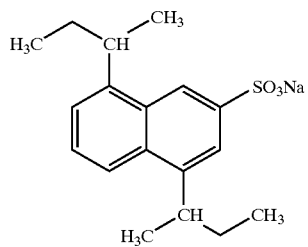

Coadd1: Compound of the formula

-continued

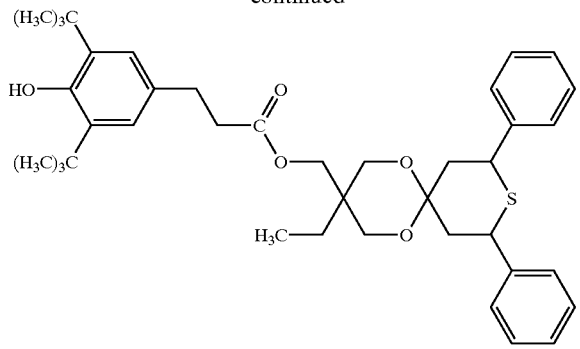

Coadd2: Compound of the formula

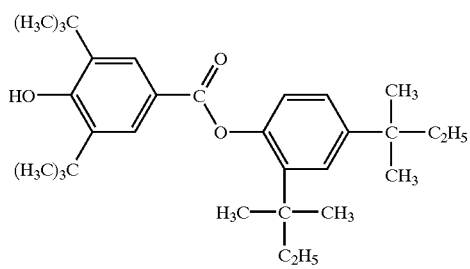

EXAMPLE III-1
Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m2).

| Component | Amount in the layer |
| --- | --- |
| Gelatine | 5150 |
| AgBr | 520 |
| Yellow coupler CoupY1 | 835 |
| Coupler solvent Solv1 | 278 |
| Additive (Table III-1) | 250 |
| Hardener Ha1 | 300 |
| Surfactant Su1 | 340 |

The layers are dried for 7 days in a ventilated cabinet. The dried samples are exposed to white light through a step-wedge of 0.3 log E exposure steps. They are developed with the P94 process for negative colour paper from ®Agfa-Gevaert, following the manufacturer's recommendations.

After exposure and processing, the remission density of the yellow dye is measured in the blue channel. The results are listed in Table III-1.

TABLE III-1

| Additive | 100 × Dmax |
| --- | --- |
| None | 206 |
| Compound of EXAMPLE 2 | 230 |
| Compound of EXAMPLE 4C | 254 |

These results show that the compounds of the present invention improve the maximal dye yield.

EXAMPLE III-2
Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m$^2$).

| Component | Amount in the layer |
| --- | --- |
| Gelatine | 5150 |
| AgBr | 520 |
| Yellow coupler CoupY2 | 854 |
| Coupler solvent Solv1 | 285 |
| Additive (Table III-2) | 256 |
| Hardener Ha1 | 300 |
| Surfactant Su1 | 340 |

The layers are dried for 7 days in a ventilated cabinet. The dried samples are exposed to white light through a step-wedge of 0.3 log E exposure steps. They are developed with the P94 process for negative colour paper from ®Agfa-Gevaert, following the manufacturer's recommendations.

After exposure and processing, the remission density of the yellow dye is measured in the blue channel. The results are listed in Table III-2.

TABLE III-2

| Additive | 100 × $D_{max}$ |
| --- | --- |
| None | 176 |
| Compound of EXAMPLE 4C | 214 |

These results show that the compounds of the present invention improve the maximal dye yield.

EXAMPLE III-3
Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m$^2$).

| Component | Amount in the layer |
| --- | --- |
| Gelatine | 5150 |
| AgBr | 520 |
| Yellow coupler CoupY1 | 835 |
| Coupler solvent Solv1 | 278 |
| Additive (Table III-3) | 250 |
| Hardener Ha1 | 300 |
| Surfactant Su1 | 340 |

The layers are dried for 7 days in a ventilated cabinet. The dried samples are exposed to white light through a step-wedge of 0.3 log E exposure steps. They are developed with the P94 process for negative colour paper from ®Agfa-Gevaert, following the manufacturer's recommendations.

After exposure and processing, the remission density of the yellow dye is measured in the blue channel. The samples are then exposed in an ®Atlas weather-O-meter so as to receive 60 kJ/cm$^2$ light energy. The temperature is 43° C.

and the relative humidity is 50%. The density loss (−ΔD) starting from a blue-density of 1 (OD=1) is determined. The results are listed in Table III-3.

TABLE III-3

| Additive | −ΔD(60 kJ/cm², from OD = 1) |
|---|---|
| None | 55 |
| Compound of EXAMPLE 2 | 28 |
| Compound of EXAMPLE 4C | 35 |
| Compound of EXAMPLE 1C | 27 |
| Compound of EXAMPLE 3 | 33 |
| Compound of EXAMPLE 5 | 33 |

These results show that the compounds of the present invention improve the light stability of yellow photographic layers.

EXAMPLE 4

Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m²).

| Component | Amount in the layer |
|---|---|
| Gelatine | 5150 |
| AgBr | 520 |
| Yellow coupler CoupY2 | 854 |
| Coupler solvent Solv1 | 285 |
| Additive (Table III-4) | 256 |
| Hardener Ha1 | 300 |
| Surfactant Su1 | 340 |

The layers are dried for 7 days in a ventilated cabinet. The dried samples are exposed to white light through a step-wedge of 0.3 log E exposure steps. They are developed with the P94 process for negative colour paper from ®Agfa-Gevaert, following the manufacturer's recommendations.

After exposure and processing, the remission density of the yellow dye is measured in the blue channel. The samples are then exposed in an ®Atlas weather-O-meter so as to receive 60 kJ/cm² light energy. The temperature is 43° C. and the relative is humidity 50%. The density loss (−ΔD) starting from a blue-density of 1 (OD=1) is determined. The results are listed in Table III-4.

TABLE III-4

| Additive | −ΔD(60 kJ/cm², from OD = 1) |
|---|---|
| None | 47 |
| Compound of EXAMPLE 2 | 26 |
| Compound of EXAMPLE 4C | 24 |
| Compound of EXAMPLE 1C | 20 |
| Compound of EXAMPLE 3 | 22 |
| Compound of EXAMPLE 5 | 22 |

These results show that compounds of the present invention improve the light stability of yellow photographic layers.

EXAMPLE III-5

Stabilization of Photographic Layers

Chromogenic photographic layers are prepared by hand-coating a gelatine emulsion containing silver bromide, yellow coupler and an additive of this invention in combination with a co-stabilizer on a polyethylene-coated paper.

The composition of the layer is as given in the following table (amounts are in mg/m²).

| Component | Amount in the layer |
|---|---|
| Gelatine | 5150 |
| AgBr | 520 |
| Yellow coupler CoupY1 | 835 |
| Coupler solvent Solv1 | 278 |
| Additive of this invention | according to Table III-5 |
| Co-stabilizer | according to Table III-5 |
| Hardener Ha1 | 300 |
| Surfactant Su1 | 340 |

The layers are dried for 7 days in a ventilated cabinet. The dried samples are exposed to white light through a step-wedge of 0.3 log E exposure steps. They are developed with the P94 process for negative colour paper from ®Agfa-Gevaert, following the manufacturer's recommendations.

After exposure and processing, the remission density of the yellow dye is measured in the blue channel. The samples are then exposed in an ®Atlas weather-O-meter so as to receive 60 kJ/cm² light energy. The temperature is 43° C. and the relative humidity is 50%. The density loss (−ΔD) starting from a blue-density of 1 (OD=1) is determined. The results are listed in Table III-5.

TABLE III-5

| Additive of this invention | mg/m² | Co-stabilizer | mg/m² | −ΔD(60 kJ/cm², from OD = 1) |
|---|---|---|---|---|
| None | | None | | 55 |
| — | | Coadd1 | 250 | 42 |
| Compound of EXAMPLE 1C | 250 | — | — | 40 |
| Compound of EXAMPLE 1C | 125 | Coadd1 | 125 | 37 |
| — | — | Coadd2 | 250 | 48 |
| Compound of EXAMPLE 1C | 125 | Coadd2 | 125 | 35 |

These results show that the compounds of the present invention improve the efficiency of classical stabilizers used in yellow photographic layers.

What is claimed is:

1. A compound of the formula (I)

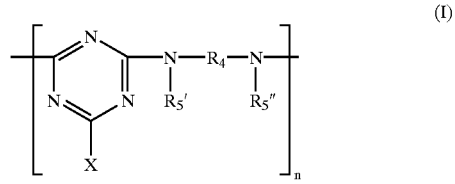

wherein $R_5'$ and $R_5''$ are a group of the formula (II);

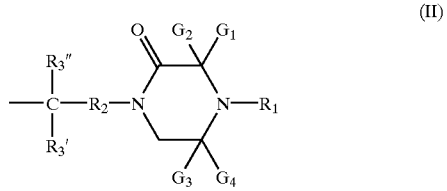

(II)

n is a number from 1 to 100;

$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$R_1$ is hydrogen, $C_1$–$C_{18}$alkyl, oxyl, —OH, —$CH_2CN$, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —$CH_2CH(OH)(G)$ with G being hydrogen, methyl or phenyl;

$R_2$ is $C_2$–$C_{14}$alkylene or a group —$CR_2'(R_2'')$— with $R_2'$ and $R_2''$ being independently of one another hydrogen, $C_1$–$C_{18}$alkyl or $C_5$–$C_{12}$cycloalkyl;

$R_3'$ and $R_3''$ are independently of one another hydrogen, $C_1$–$C_{18}$alkyl, $C_2$–$C_{18}$alkyl interrupted by oxygen; or $C_5$–$C_{12}$cycloalkyl;

$R_4$ is $C_2$–$C_{14}$alkylene, $C_4$–$C_{14}$alkylene interrupted by oxygen or sulphur; $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi-($C_1$–$C_4$alkylene);

X is —$OR_6$, —$SR_6$, —$N(R_7)(R_8)$ or a group of the formula (IV);

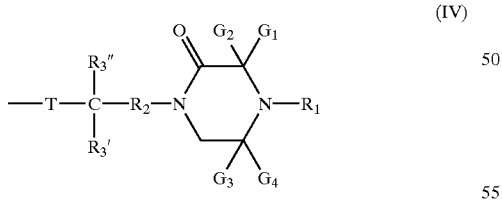

(IV)

$R_6$, $R_7$ and $R_8$ are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_{12}$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_8$alkoxy, di($C_1$–$C_4$alkyl)amino or a group of the formula (III);

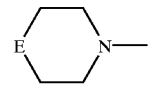

(III)

with E being a direct bond, —O—, —$CH_2$—, —$CH_2CH_2$— or >N—$CH_3$;

or —$N(R_7)(R_8)$ is additionally a group of the formula (III);

T is —O— or >N—$R_9$; and $R_9$ is hydrogen, $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by $C_1$–$C_8$alkoxy, di($C_1$–$C_4$alkyl)amino or a group of the formula (III);

the radicals $R_1$, the radicals $R_2$, the radicals $R_3'$, the radicals $R_3''$, the radicals $G_1$, the radicals $G_2$, the radicals $G_3$ or the radicals $G_4$, independently of one another, have the same or a different meaning; and in the individual recurrent units of the formula (I), each of the radicals X, $R_4$, $R_5'$ and $R_5''$ has the same or a different meaning.

2. A compound according to claim 1 wherein $G_1$, $G_2$, $G_3$ and $G_4$ are independently of one another $C_1$–$C_6$alkyl or cyclohexyl or the radicals $G_1$ and $G_2$ and the radicals $G_3$ and $G_4$ form independently of one another, together with the carbon atom they are attached to, cyclohexyl;

$R_2$ is $C_2$–$C_8$alkylene or a group —$CR_2'(R_2'')$— with $R_2'$ and $R_2''$ being independently of one another hydrogen, $C_1$–$C_8$alkyl or $C_5$–$C_8$cycloalkyl;

$R_3'$ and $R_3''$ are independently of one another hydrogen, $C_1$–$C_8$alkyl, $C_2$–$C_8$alkyl interrupted by oxygen; or $C_5$–$C_8$cycloalkyl;

$R_4$ is $C_2$–$C_{10}$alkylene, $C_4$–$C_{10}$alkylene interrupted by oxygen or sulphur; cyclohexylene, cyclohexylenedi($C_1$–$C_4$alkylene), $C_1$–$C_4$alkylenedi(cyclohexylene) or phenylenedi($C_1$–$C_4$alkylene);

$R_5'$ and $R_5''$ are a group of the formula (II);

$R_6$, $R_7$ and $R_8$ are independently of one another hydrogen, $C_1$–$C_8$alkyl, $C_3$–$C_{12}$alkenyl, $C_5$–$C_8$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_{12}$phenylalkyl; tetrahydrofurfuryl or $C_2$–$C_4$alkyl which is substituted in the 2, 3 or 4 position by $C_1$–$C_4$alkoxy, di($C_1$–$C_4$alkyl) amino or a group of the formula (III);

or —$N(R_7)(R_8)$ is additionally a group of the formula (III); and $R_9$ is hydrogen, $C_1$–$C_8$alkyl, $C_2$–$C_8$hydroxyalkyl, $C_3$–$C_{12}$alkenyl, $C_5$–$C_8$cycloalkyl which is unsubstituted or substituted by 1, 2 or 3 $C_1$–$C_4$alkyl; $C_7$–$C_{12}$phenylalkyl; tetrahydrofurfuryl, a group of the formula (II), or $C_2$–$C_4$alkyl which is substituted in the 2, 3 or 4 position by $C_1$–$C_4$alkoxy, di($C_1$–$C_4$alkyl) amino or a group of the formula (III).

3. A compound according to claim 1 wherein $G_1$, $G_2$, $G_3$ and $G_4$ are independently of one another $C_1$–$C_4$alkyl;

R$_2$ is C$_2$–C$_4$alkylene or a group —CR$_2$'(R$_2$")— with R$_2$' and R$_2$" being independently of one another hydrogen or C$_1$–C$_4$alkyl;

R$_3$' and R$_3$" are independently of one another hydrogen or C$_1$–C$_4$alkyl;

R$_4$ is C$_2$–C$_{10}$alkylene;

R$_5$' and R$_5$" are a group of the formula (II);

X is —N(R$_7$)(R$_8$) or a group of the formula (IV);

R$_7$ and R$_8$ are independently of one another hydrogen or C$_1$–C$_8$alkyl;

or —N(R$_7$)(R$_8$) is additionally a group of the formula (III) with E being —O—; and R$_9$ is hydrogen, C$_1$–C$_8$alkyl or cyclohexyl.

4. A compound according to claim 1 wherein n is a number from 2 to 50.

5. A compound according to claim 1 wherein the radicals R$_1$ are independently of one another hydrogen, C$_1$–C$_4$alkyl, —OH, allyl, C$_1$–C$_{12}$alkoxy, C$_5$–C$_8$cycloalkoxy, benzyl or acetyl.

6. A compound according to claim 1 wherein G$_1$, G$_2$, G$_3$ and G$_4$ are independently of one another C$_1$–C$_4$alkyl.

7. A compound according to claim 1 wherein R$_3$' is hydrogen.

8. A compound according to claim 1 wherein n is a number from 2 to 50;

G$_1$, G$_2$, G$_3$ and G$_4$ are independently of one another C$_1$–C$_4$alkyl;

R$_1$ is hydrogen or C$_1$–C$_4$alkyl;

R$_2$ is methylene;

R$_3$' is hydrogen and R$_3$" is hydrogen or C$_1$–C$_4$alkyl;

R$_4$ is C$_2$–C$_8$alkylene;

R$_5$' and R$_5$" are a group of the formula (II); and

X is —N(R$_7$)(R$_8$) with R$_7$ and R$_8$ being independently of one another hydrogen or C$_1$–C$_8$alkyl.

9. A compound according to claim 1, which corresponds to the formula

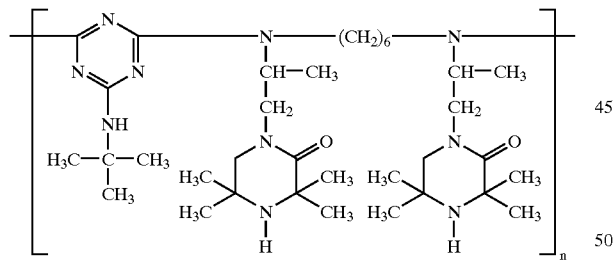

with n being a number from 2 to 50.

10. A composition containing an organic material susceptible to degradation induced by light, heat or oxidation and at least one compound of the formula (I) according to claim 1.

11. A composition according to claim 10 wherein the organic material is a synthetic polymer.

12. A composition according to claim 10 wherein the organic material is a polyolefin.

13. A composition according to claim 10 wherein the organic material is a polycarbonate, a thermoplastic polyurethane or a polyacetal.

14. A method for stabilizing an organic material against degradation induced by light, heat or oxidation, which comprises incorporating into said organic material at least one compound of the formula (I) according to claim 1.

15. A composition containing an organic material susceptible to degradation induced by light, heat or oxidation and at least one compound of the formula (I)

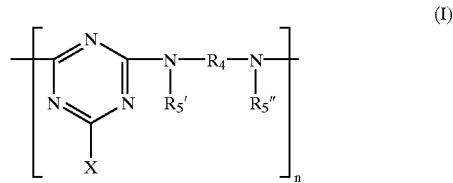

wherein at least one group of the formula (II)

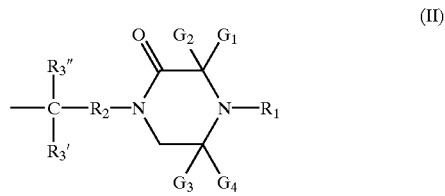

is present in the repeating unit of the formula (I);

n is a number from 1 to 100;

G$_1$, G$_2$, G$_3$ and G$_4$ are independently of one another C$_1$–C$_{18}$alkyl or C$_5$–C$_{12}$cycloalkyl or the radicals G$_1$ and G$_2$ and the radicals G$_3$ and G$_4$ form independently of one another, together with the carbon atom they are attached to, C$_5$–C$_{12}$cycloalkyl;

R$_1$ is hydrogen, C$_1$–C$_{18}$alkyl, oxyl, —OH, —CH$_2$CN, C$_3$–C$_6$alkenyl, C$_3$–C$_8$alkynyl, C$_7$–C$_{12}$phenylalkyl unsubstituted or substituted on the phenyl by 1, 2 or 3 C$_1$–C$_4$alkyl or C$_1$–C$_4$alkoxy; C$_1$–C$_8$acyl, C$_1$–C$_{18}$alkoxy, C$_5$–C$_{12}$cycloalkoxy, C$_7$–C$_{12}$phenylalkoxy unsubstituted or substituted on the phenyl by 1, 2 or 3 C$_1$–C$_4$alkyl or C$_1$–C$_4$alkoxy; C$_1$–C$_{18}$alkanoyloxy, (C$_1$–C$_{18}$alkoxy)carbonyl, glycidyl or a group —CH$_2$CH(OH)(G) with G being hydrogen, methyl or phenyl;

R$_2$ is C$_2$–C$_{14}$alkylene or a group —CR$_2$'(R$_2$")— with R$_2$' and R$_2$" being independently of one another hydrogen, C$_1$–C$_{18}$alkyl or C$_5$–C$_{12}$cycloalkyl;

R$_3$' and R$_3$" are independently of one another hydrogen, C$_1$–C$_{18}$alkyl, C$_2$–C$_{18}$alkyl interrupted by oxygen; or C$_5$–C$_{12}$cycloalkyl;

R$_4$ is C$_2$–C$_{14}$alkylene, C$_4$–C$_{14}$alkylene interrupted by oxygen or sulphur; C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene) or phenylenedi-(C$_1$–C$_4$alkylene);

R$_5$' and R$_5$" are independently of one another hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_{12}$phenylalkyl which is unsubstituted or substituted on the phenyl by 1, 2 or 3 C$_1$–C$_4$alkyl;

tetrahydrofurfuryl, a group of the formula (II) or C₂–C₄alkyl which is substituted in the 2, 3 or 4 position by —OH, C₁–C₈alkoxy, di(C₁–C₄alkyl)amino or a group of the formula (III);

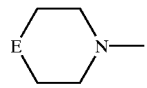

with E being a direct bond, —O—, —CH₂—, —CH₂CH₂— or >N—CH₃;

X is —OR₆, —SR₆, —N(R₇)(R₈) or a group of the formula (IV);

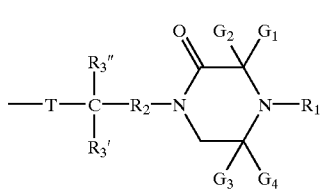

R₆, R₇ and R₈ are independently of one another hydrogen, C₁–C₁₈alkyl, C₃–C₁₈alkenyl, C₅–C₁₂cycloalkyl which is unsubstituted or substituted by 1, 2 or 3 C₁–C₄alkyl; phenyl which is unsubstituted or substituted by 1, 2 or 3 C₁–C₄alkyl or C₁–C₄alkoxy; C₇–C₁₂phenylalkyl which is unsubstituted or substituted on the phenyl by 1, 2 or 3 C₁–C₄alkyl; tetrahydrofurfuryl or C₂–C₄alkyl which is substituted in the 2, 3 or 4 position by C₁–C₈alkoxy, di(C₁–C₄alkyl)amino or a group of the formula (III);

or —N(R₇)(R₈) is additionally a group of the formula (III);

T is —O— or >N—R₉; and

R₉ is hydrogen, C₁–C₁₈alkyl, C₂–C₁₈hydroxyalkl, C₃–C₁₈alkenyl, C₅–C₁₂cycloalkyl which is unsubstituted or substituted by 1, 2 or 3 C₁–C₄alkyl; C₇–C₁₂phenylalkyl which is unsubstituted or substituted on the phenyl by 1, 2 or 3 C₁–C₄alkyl; tetrahydrofurfuryl, a group of the formula (II), or C₂–C₄alkyl which is substituted in the 2, 3 or 4 position by C₁–C₈alkoxy, di(C₁–C₄alkyl)amino or a group of the formula (III);

the radicals R₁, the radicals R₂, the radicals R₃', the radicals R₃", the radicals G₁, the radicals G₂, the radicals G₃ or the radicals G₄, independently of one another, have the same or a different meaning; and in the individual recurrent units of the formula (I), each of the radicals X, R₄, R₅' and R₅" has the same or a different meaning;

with the proviso that one of the radicals R₅' and R₅" is different from hydrogen, when X is a group of the formula (IV) with T being >N—R₉ wherein the organic material is a thermoplastic rubber.

16. A recording material containing at least one compound of the formula (I)

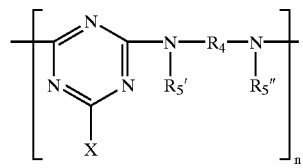

wherein
at least one group of the formula (II)

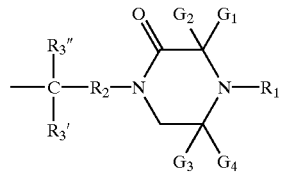

is present in the repeating unit of the formula (I);
n is a number from 1 to 100;
G₁, G₂, G₃ and G₄ are independently of one another C₁–C₁₈alkyl or C₅–C₁₂cycloalkyl or the radicals G₁ and G₂ and the radicals G₃ and G₄ form independently of one another, together with the carbon atom they are attached to, C₅–C₁₂cycloalkyl;
R₁ is hydrogen, C₁–C₁₈alkyl, oxyl, —OH, —CH₂CN, C₃–C₆alkenyl, C₃–C₈alkynyl, C₇–C₁₂phenylalkyl unsubstituted or substituted on the phenyl by 1, 2 or 3 C₁–C₄alkyl or C₁–C₄alkoxy; C₁–C₈acyl, C₁–C₁₈alkoxy, C₅–C₁₂cycloalkoxy, C₇–C₁₂phenylalkoxy unsubstituted or substituted on the phenyl by 1, 2 or 3 C₁–C₄alkyl or C₁–C₄alkoxy; C₁–C₁₈alkanoyloxy, (C₁–C₁₈alkoxy)carbonyl, glycidyl or a group —CH₂CH(OH)(G) with G being hydrogen, methyl or phenyl;
R₂ is C₂–C₁₄alkylene or a group —CR₂'(R₂")— with R₂' and R₂" being independently of one another hydrogen, C₁–C₁₈alkyl or C₅–C₁₂cycloalkyl;
R₃' and R₃" are independently of one another hydrogen, C₁–C₁₈alkyl, C₂–C₁₈alkyl interrupted by oxygen; or C₅–C₁₂cycloalkyl;
R₄ is C₂–C₁₄alkylene, C₄–C₁₄alkylene interrupted by oxygen or sulphur; C₅–C₇cycloalkylene, C₅–C₇cycloalkylenedi(C₁–C₄alkylene), C₁–C₄alkylenedi(C₅–C₇cycloalkylene) or phenylenedi-(C₁–C₄alkylene);
R₅' and R₅" are independently of one another hydrogen, C₁–C₁₈alkyl, C₃–C₁₈alkenyl, C₅–C₁₂cycloalkyl which is unsubstituted or substituted by 1, 2 or 3 C₁–C₄alkyl; C₇–C₁₂phenylalkyl which is unsubstituted or substituted on the phenyl by 1, 2 or 3 C₁–C₄alkyl; tetrahydrofurfuryl, a group of the formula (II) or C₂–C₄alkyl which is substituted in the 2, 3 or 4 position by —OH, C₁–C₈alkoxy, di(C₁–C₄alkyl)amino or a group of the formula (III);

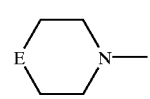

with E being a direct bond, —O—, —CH₂—, —CH₂CH₂— or >N—CH₃;

X is —OR$_6$, —SR$_6$, —N(R$_7$)(R$_8$) or a group of the formula (IV);

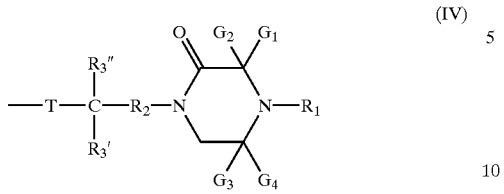

(IV)

R$_6$, R$_7$ and R$_8$ are independently of one another hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$–C$_4$alkoxy; C$_7$–C$_{12}$phenylalkyl which is unsubstituted or substituted on the phenyl by 1, 2 or,3 C$_1$–C$_4$alkyl; tetrahydrofurfuryl or C$_2$–C$_4$alkyl which is substituted in the 2, 3 or 4 position by C$_1$–C$_8$alkoxy, di(C$_1$–C$_4$alkyl)amino or a group of the formula (III);

or —N(R$_7$)(R$_8$) is additionally a group of the formula (III);

T is —O— or >N—R$_9$; and

R$_9$ is hydrogen, C$_1$–C$_{18}$alkyl, C$_2$–C$_{18}$hydroxyalkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_{12}$phenylalkyl which is unsubstituted or substituted on the phenyl by 1, 2 or 3 C$_1$–C$_4$alkyl; tetrahydrofurfuryl, a group of the formula (II), or C$_2$–C$_4$alkyl which is substituted in the 2, 3 or 4 position by C$_1$–C$_8$alkoxy, di(C$_1$–C$_4$alkyl)amino or a group of the formula (III);

the radicals R$_1$, the radicals R$_2$, the radicals R$_3$', the radicals R$_3$", the radicals G$_1$, the radicals G$_2$, the radicals G$_3$ or the radicals G$_4$, independently of one another, have the same or a different meaning; and in the individual recurrent units of the formula (I), each of the radicals X, R$_4$, R$_5$' and R$_5$" has the same or a different meaning;

with the proviso that one of the radicals R$_5$' and R$_5$" is different from hydrogen, when X is a group of the formula (IV) with T being >N—R$_9$.

17. A recording material according to claim 16, corresponding to a photographic material comprising on a substrate at least one layer containing a compound of the formula (I).

18. A recording material according to claim 16, corresponding to a silver halide colour photographic material comprising a support having thereon at least one light-sensitive silver halide emulsion layer and optionally a non-light sensitive emulsion layer, characterized in that at least one light-sensitive layer contains a compound of the formula (I).

19. A compound of the formula (Z-1)

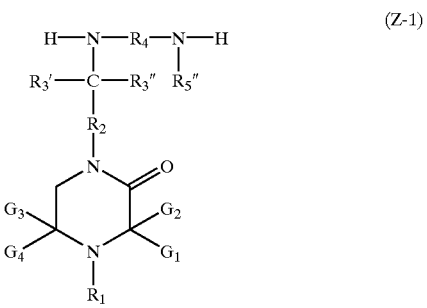

(Z-1)

wherein

G$_1$, G$_2$, G$_3$ and G$_4$ are independently of one another C$_1$–C$_{18}$alkyl or C$_5$–C$_{12}$cycloalkyl or the radicals G$_1$ and G$_2$ and the radicals G$_3$ and G$_4$ form independently of one another, together with the carbon atom they are attached to, C$_5$–C$_{12}$cycloalkyl;

R$_1$ is hydrogen, C$_1$–C$_{18}$alkyl, oxyl, —OH, —CH$_2$CN, C$_3$–C$_6$alkenyl, C$_3$–C$_8$alkynyl, C$_7$–C$_{12}$phenylalkyl unsubstituted or substituted on the phenyl by 1, 2 or 3 C$_1$–C$_4$alkyl or C$_1$–C$_4$alkoxy; C$_1$–C$_8$acyl, C$_1$–C$_{18}$alkoxy, C$_5$–C$_{12}$cycloalkoxy, C$_7$–C$_{12}$phenylalkoxy unsubstituted or substituted on the phenyl by 1, 2 or 3 C$_1$–C$_4$alkyl or C$_1$–C$_4$alkoxy; C$_1$–C$_{18}$alkanoyloxy, glycidyl or a group —CH$_2$CH(OH)(G) with G being hydrogen, methyl or phenyl;

R$_2$ is C$_2$–C$_{14}$alkylene or a group —CR$_2$'(R$_2$")— with R$_2$' and R$_2$" being independently of one another hydrogen, C$_1$–C$_{18}$alkyl or C$_5$–C$_{12}$cycloalkyl;

R$_3$' and R$_3$" are independently of one another hydrogen, C$_1$–C$_{18}$alkyl, C$_2$–C$_{18}$alkyl interrupted by oxygen or C$_5$–C$_{12}$cycloalkyl;

R$_4$ is C$_2$–C$_{14}$alkylene, C$_4$–C$_{14}$alkylene interrupted by oxygen or sulphur; C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene) or phenylenedi(C$_1$–C$_4$alkylene);

R$_5$' is hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_{12}$phenylalkyl which is unsubstituted or substituted on the phenyl by 1, 2 or 3 C$_1$–C$_4$alkyl; tetrahydrofurfuryl, a group of the formula (II)

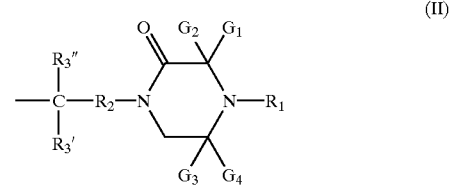

(II)

or $C_2$–$C_4$alkyl which is substituted in the 2, 3 or 4 position by —OH, $C_1$–$C_8$alkoxy, di($C_1$–$C_4$alkyl)amino or a group of the formula (III);

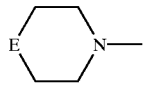

(III)

with E being —O—, —$CH_2$—, —$CH_2CH_2$— or >N—$CH_3$.

20. A compound according to claim 19, which corresponds to the formula

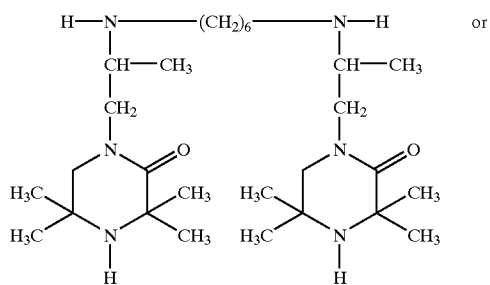

or

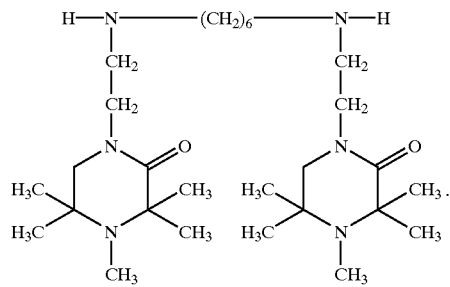

21. A compound of the formula (Z-2)

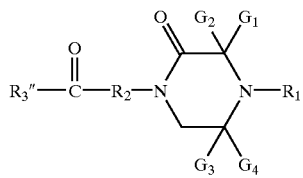

(Z-2)

wherein
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;
$R_1$ is hydrogen, $C_1$–$C_{18}$alkyl, oxyl, —OH, —$CH_2CN$, $C_3$–$C_6$alkenyl, $C_3$–$C_4$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, glycidyl or a group —$CH_2CH(OH)(G)$ with G being hydrogen, methyl or phenyl;
$R_2$ is $C_2$–$C_{14}$alkylene or a group —$CR_2'(R_2'')$— with $R_2'$ and $R_2''$ being independently of one another hydrogen, $C_1$–$C_{18}$alkyl or $C_5$–$C_{12}$cycloalkyl; and
$R_3''$ is hydrogen, $C_1$–$C_{18}$alkyl, $C_2$–$C_{18}$alkyl interrupted by oxygen; or $C_5$–$C_{12}$cycloalkyl.

22. A compound according to claim 21, which corresponds to the formula

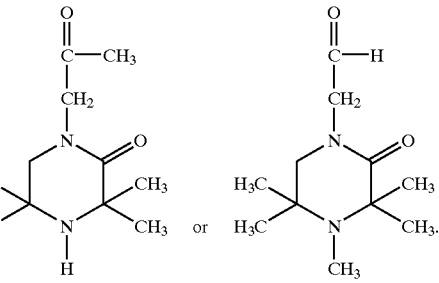

* * * * *